(12) United States Patent
Carney et al.

(10) Patent No.: US 7,675,616 B1
(45) Date of Patent: Mar. 9, 2010

(54) COMBUSTION PLUME ABSORPTION GAUGE

(75) Inventors: Joel R. Carney, La Plata, MD (US); John Wilinson, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 101 days.

(21) Appl. No.: 11/974,000

(22) Filed: Sep. 19, 2007

(51) Int. Cl.
*G01J 3/42* (2006.01)

(52) U.S. Cl. .................. 356/326; 356/437; 356/438

(58) Field of Classification Search ............. 356/436, 356/437, 438
See application file for complete search history.

(56) References Cited

U.S. PATENT DOCUMENTS

| | | | |
|---|---|---|---|
| 2,580,500 A * | 1/1952 | Albert .................. 356/442 |
| 4,018,635 A | 4/1977 | Ryan et al. |
| 4,688,943 A * | 8/1987 | Modarress .............. 356/436 |
| 4,786,171 A * | 11/1988 | LeFebre et al. .......... 356/326 |
| 4,998,017 A | 3/1991 | Ryan et al. |
| 5,046,854 A | 9/1991 | Weller et al. |
| 5,335,067 A | 8/1994 | Prather et al. |
| 5,402,241 A | 3/1995 | Jeannotte et al. |
| 5,657,404 A | 8/1997 | Buchanan et al. |
| 5,678,751 A | 10/1997 | Buchanan et al. |
| 5,978,534 A | 11/1999 | O'Rourke et al. |
| 6,078,042 A | 6/2000 | Fellows |
| 6,115,528 A | 9/2000 | Schumacher et al. |
| 6,188,474 B1 | 2/2001 | Dussault et al. |
| 6,188,475 B1 | 2/2001 | Inman et al. |
| 6,205,272 B1 | 3/2001 | O'Rourke et al. |
| 6,292,610 B1 | 9/2001 | O'Rourke et al. |
| 6,396,056 B1 | 5/2002 | Lord et al. |
| 6,515,748 B2 | 2/2003 | Walker et al. |
| 6,603,555 B1 | 8/2003 | Nanami et al. |
| 6,603,556 B2 | 8/2003 | Belz et al. |
| 6,750,453 B1 | 6/2004 | Nelson et al. |
| 6,795,190 B1 | 9/2004 | Paul et al. |
| 6,862,091 B2 | 3/2005 | Johnson |
| 6,995,846 B2 | 2/2006 | Kalayeh et al. |
| 7,057,720 B2 | 6/2006 | Caracci et al. |
| 7,075,653 B1 | 7/2006 | Rutherford |
| 7,084,963 B2 | 8/2006 | Leipertz |
| 7,092,089 B2 | 8/2006 | Filippini et al. |

* cited by examiner

*Primary Examiner*—F. L Evans
(74) *Attorney, Agent, or Firm*—Fredric J. Zimmerman

(57) ABSTRACT

An absorption spectroscopy gauge to measure chemical concentrations in a post-detonation combustion cloud of energetic materials. A broadband light source coupled to an optical fiber guides light into a gauge via a first leg where a plano-convex lens collimates the light source internally. The light reflects off a mirror and passes through an absorption region before entering a second leg of the gauge where it is refocused into a different fiber and sent to a time-resolved spectroscopy system for analysis. The time-resolved spectroscopy system can include a spectrometer and a steak camera. The two legs of the gauge are arranged as separate halves connected by a plurality of rods that can be adjusted to change the length of the absorption region. The gauge is arranged to include stainless steel cone shaped tips to minimize added turbulence brought upon by its use.

3 Claims, 1 Drawing Sheet

COMBUSTION PLUME ABSORPTION GAUGE

STATEMENT OF GOVERNMENT INTEREST

The invention described herein may be manufactured and used by or for the Government of the United States of America for Governmental purposes without the payment of any royalties thereon or therefore.

FIELD OF THE INVENTION

The present invention is directed to time-resolved absorption spectroscopy.

BACKGROUND OF THE INVENTION

Spectroscopic analysis provides information about the identity, structure, and concentration of the chemical species of a given sample using the detected energy change of an atom or molecule through either the emission or absorption of a photon. Absorption spectroscopy measures the net absorption of incident radiation throughout a chosen wavelength range. Radiation passing through a sample is attenuated depending upon the path length traveled by the radiation, the strength and concentration of absorbing species present and scattering losses. Unique spectral fingerprints arise from the absorption of photons of light at discrete (resonant) energies, signifying known electronic, vibrational and/or rotational energetic transitions. A plot of light absorbance or transmission versus wavelength for a given sample is used to map out the spectral fingerprints for species identification.

In general for absorption spectroscopy, an arrangement of light sources, fiber optics, mirrors, collimating lens and spectrometers are used to direct light through a given sample or interaction region, to collect the light emerging from the sample and to analyze the collected light. A given absorption spectroscopy system is sensitive to the sample and environment studied. In general, however, absorption spectroscopy systems are not constructed for use in hazardous environments where the systems or probes would experience elevated temperatures and pressures.

A known arrangement for use in hostile environments is a Raman fiber optic probe assembly. In this case, the hostile environment is an autoclave, and the probe forms a dry well assembly. The probe is positioned inside a shell and supported by a hanger pipe. The arrangement of the probe makes it suitable for pressures up to 2000 psi and temperatures up to 600° F. However, the probe is isolated from the hazardous environment and requires sturdy structures to provide this physical isolation.

Other arrangements of apparati for spectroscopic analysis in hazardous environments are disclosed in the related art. However, the arrangements are application specific, and no device is arranged for measuring the post-detonation combustion cloud of energetic materials, and in particular for providing a probe or gauge that can be placed within the detonation cloud to analyze the species in the cloud in particular over the very brief time period associated with a detonation event.

SUMMARY OF THE INVENTION

The present invention provides for gauges used for absorption spectroscopy in hostile environments and, in particular, in the blast zone of energetic materials. A broadband light source extending over the wavelength region of interest, as defined by the known optical signatures of the chemical transients being investigated, is coupled into an optical fiber. The optical fiber guides the light into a first leg or portion of the gauge. The first portion of the gauge includes a first plano-convex lens to collimate the incident light from the light source. In one embodiment, singlet lenses are used when the light source is at a single frequency as in a narrowband laser, while achromatic doublets are utilized for manipulating broadband light sources. The collimated light is then reflected by a mirror through the interaction or absorption region where it interacts with the sample being tested. After passing through the absorption region, the light enters the second portion or leg of the gauge where it is reflected by a second mirror into a lens that focuses the collimated light into a second optical fiber. The second optical fiber delivers the post-absorption light to a time-resolved spectroscopy system for analysis.

The time-resolved spectroscopy system includes a spectrometer in communication with the second optical fiber. The spectrometer provides wavelength dispersion of the light and is in communication with a time-resolved data recording device. Examples of such devices are fast framing cameras, light-sensitive arrays and streak cameras. The choice of data collection device depends on the time requirements of the experiment. Each will result in a set of spectra that are representative of a particular time step. The gauge in combination with the time-resolved spectroscopy system produces an image of data that is sensitive to small changes in the light intensity (for example the laser beam intensity) as a function of time. These changes in the light beam intensity can result from atoms or molecules in the sample disposed within the absorption region of the gauge that preferentially, i.e., resonantly, absorb light at a particular frequency. Changes in light intensity can also arise from the non-resonant scattering of light from particulate matter in the sample. The changes attributable to non-resonant scattering can be ascertained using a reference light source, such as an off-resonance narrowband laser, or the background, non-resonant signal of a broadband light source. The amount of light absorbed is directly related to the concentration of particular transients in the sample following the Beer-Lambert equation.

In accordance with one method for using the gauge to measure transient species in a combustion plume, the interaction or absorption region of the gauge is placed a known distance from an explosive charge. The time-resolved spectroscopy equipment collects the light source as a function of time, monitoring the change in the light signal that is observed when atomic and molecular decomposition products from the explosive event traverse the interaction region of the gauge.

Each gauge has a generally elongated shape and at least a portion of the elongated shape utilizes the pencil form, having a tapered or conical shape. When placed a known distance from the explosive charge, the pencil form of each leg is positioned to point towards the charge to minimize the turbulence that is added to the combustion environment by the presence of the gauge itself. The two portions of the gauge, forming two separate or independent halves, are connected by an adjustable attachment mechanism, for example four small posts. The legs of the gauge, when connected by the posts, define the length of the absorption region. The attachment between the legs and the posts is adjustable. This adjustment changes the distance between the legs and, therefore, the length of the interaction or absorption region between them, i.e., the pathlength, which has an effect on the spectroscopic analysis of the sample.

BRIEF DESCRIPTION OF THE DRAWINGS

In the drawings, which are not necessarily to scale, like or corresponding parts are denoted by like or corresponding reference numerals.

DETAILED DESCRIPTION

Figure 1:
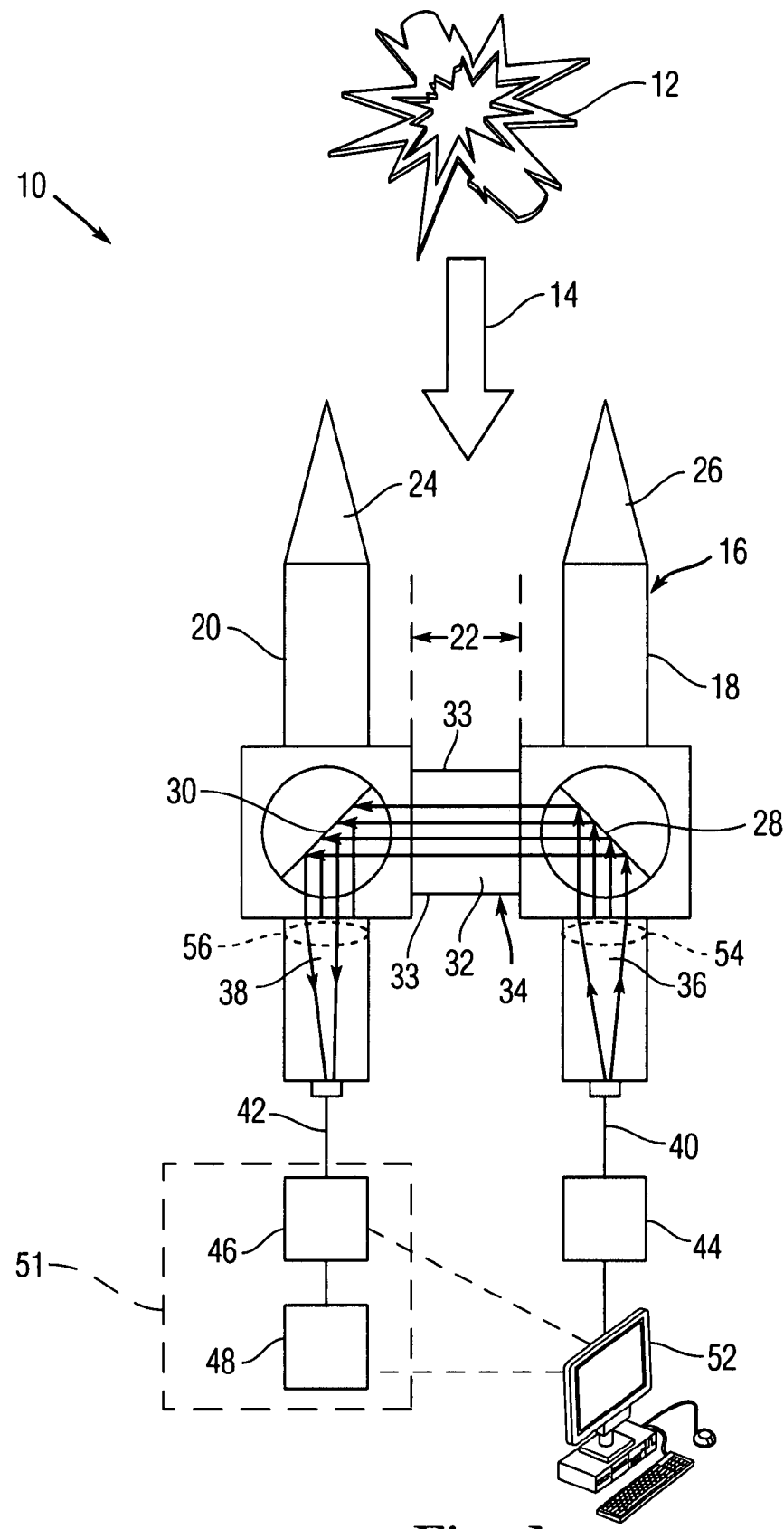
FIG. 1 is a schematic representation of an embodiment of an absorption gauge in accordance with the present invention disposed in an exemplary application.

Referring to FIG. 1, an exemplary embodiment of a system 10 for measuring atomic and molecular decomposition products of an explosive event utilizing an absorption spectroscopy gauge 16 in accordance with the present invention is illustrated. The system 10 includes at least one absorption spectroscopy gauge 16 in communication with a light source 44 and a time-resolved spectroscopy system 51. The time-resolved spectroscopy system 51 includes a spectrometer 46 to produce a wavelength dispersion of the incoming light across the wavelengths of interest. The spectrometer is in communication with, and delivers the wavelength-dispersed light to, time-resolved detector such as a camera or array 48. If very fast time-scales are probed (for example, having a sub-microsecond time resolution), the camera can be a streak unit to amplify and to disperse the light temporally. Therefore, the time-resolved spectroscopy system 51 can produce a time-resolved profile of the non-absorbed light passing through the gauge 16 in time periods associated with the detonation of energetic materials. Suitable spectrometers and streak cameras are known and available in the art.

Suitable light sources include broadband light sources (halogen lamps and pulsed flashlights) and narrowband light sources (lasers). The light source and all of the components in the time-resolved spectroscopy system 51 are in communication with a computing system 52 that can control the various components and can receive, analyze and store data form the time-resolved spectroscopy system. In general, any light source that can deliver wavelengths of light appropriate for absorption by the chemical species that are being measured in the absorption region of the gauge 16 can be used. The required intensity of the light source will be dictated by the expected opacity of the interaction region and the desired time resolution.

The light source 44 is in communication with the gauge 16 through a first fiber optic cable 40, and the time-resolved spectroscopy system 51 is in communication with the gauge 16 through a second fiber optic cable 42.

In one embodiment, the gauge 16 includes at least two portions, a first portion 18 or leg and a second portion 20 or leg. Suitable materials for first and second portions 18 and 20 include any material capable of withstanding the heat and pressure found in an area adjacent the detonation of an energetic material. These materials include metals, ceramics, polymers and combinations thereof. More particularly, the first and second portions 18 and 20 are constructed from stainless steel. The first portion 18 includes a first optical path 36, through which light can be transmitted. This first optical path 36 includes at least one lens 54 and at least one mirror 28. More particularly, the lens 54 is a collimating lens such as a plano-convex lens, and the mirror 28 is a plane mirror. The properties of the plano-convex lens depend on the spectral properties of the light source used. The second portion 20 includes a second optical path 38 passing there through. Disposed within the second optical path 38 is at least one lens 56 and at least one mirror 30. The lens 54 is preferably a collimating lens such as a plano-convex lens, and the mirror 30 is a plane mirror. Achromatic lenses are suggested for properly collimating a broadband source while single element piano-convex lenses are adequate for single frequency, narrowband lasers.

The first and second portions 18 and 20 are attached together to form an interaction or absorption region 32 between the two portions. The absorption region 32 receives a sample of the materials from the detonation event and a light from the light source to pass through this sample, where the light is absorbed based by the various species of that sample. In one embodiment, the first and second portions 18 and 20 are attached together so that the length 22 of the absorption region 32 is fixed. Alternatively, the length of the absorption region 32 can be varied since the absorption of light is affected by the path length of the light through the material, i.e. the length 22 of the absorption region 32. In one embodiment, the gauge 16 includes an attachment mechanism 34 attached to both the first and second portions. More particularly, the attachment mechanism 34 is an adjustable attachment mechanism. An adjustable attachment mechanism permits the length 22 of the absorption region to be varied. Therefore, the adjustable attachment mechanism 34 allows the first and second portions 18 and 20 to move relative to one another. For example, the attachment mechanism 34 can be a telescoping or expandable mechanism. In one embodiment, the attachment mechanism is threaded into each one of the first and second portions, and the amount that each portion is threaded onto the attachment mechanism 34 defines the length 22 of the absorption region 32. In one embodiment, the attachment mechanism 34 includes a plurality of rods 33. For example the gauge 16 can contain at least two rods 33. In another embodiment, the gauge 16 includes four rods 33. Each rod 33 has two ends, and each end of a given rod attached to one of the first or second portions 18 and 20 of the gauge 16. Suitable materials for the rods 33 are the same as for the first and second portions 18 and 20.

The first and second portions 18 and 20 when attached together, either fixedly or adjustably using the attachment mechanism 34, are attached such that the first optical path 36 is aligned with the second optical path 38. The optical paths 36 and 38 are aligned through the absorption region 32 between the first and second portions 18 and 20 such that light passing through the first optical path 36 travels through the absorption region 32 to the second optical path 38.

In one embodiment, at least one and more particularly, both of the first and second portions 18 and 20 have a generally elongated shape. This shape minimizes the effect of the gauge 16 on the detonation cloud that is being measured. As illustrated in one embodiment, the first and second portions 18 and 20 are mirror images of one another. In order to further reduce the profile and effect of the gauge on the detonation cloud, the first portion 18 comprises a tapered or conical shaped portion 26 and the second portion 20 comprises a tapered or conical shaped portion 24. Therefore, each portion of the gauge 16 can be said to have a pencil shape. In one embodiment, the cone shaped tips are made of stainless steel and taper from a diameter of about 1 inch to a point over a length of about 2 inches. The first and second optical paths 36 and 38 pass through 2-inch length by 1-inch diameter lens tubes and cubes. Suitable lens tubes and cubes are known and available in the art. In general, the dimensions of the gauge 16 are test dependent and can be varied accordingly.

In use, the gauge 16 is placed in proximity to a charge of energetic material, such that upon detonation, the detonation cloud will be within or will traverse the absorption region of the gauge. In one embodiment, the gauge 16 is placed such that the tapered ends 24 and 26 of each portion are pointing in the direction of the detonation event 12 and are aligned generally parallel with a direction of propagation 14 of the detonation cloud from that event. Therefore, the detonation cloud will encompass the absorption region 32 of the gauge, and the species of the cloud can be measured. The light source 44 and measuring equipment can be located a sufficient distance away from the detonation event. Light from the light source 44 is delivered to the first portion 18 through the first optical fiber 40 which is in communication with the first portion 18. The light travels through the first optical path 36, passing through the collimating lens 54 and reflected through the absorption region 32 by the mirror 28. The light passes through the absorption region 32 and is incident upon the mirror 30 in the second optical path 38 of the second portion 20. This mirror 30 reflects the post-absorption light to the collimating lens 56 where it is focused onto a second optical fiber 42 in communication with the second portion 20. This second optical fiber 42 transmits the light to the time-resolved spectroscopy system 51 where it is analyzed. More particularly, the first and second optical fibers 40 and 42 are connected to the first and second portions 18 and 20 opposite from the tapered ends 24 and 26, to minimize the effects of the detonation on these components. In addition, the length of the absorption region 32 is set based upon the desired path length 22 for absorption.

In one embodiment, the system utilizes Raman spectroscopy or Terahertz spectroscopy. Non-linear Raman spectroscopy or Terahertz spectroscopy can also probe spectrally-specific signatures with spatial sensitivity. Non-linear Raman signals, however, are more significantly affected by the sooty, non-resonant light scattering that is inherent in post-detonation clouds. Terahertz measurements are currently limited in time resolution and require a very expensive light source and non-standard optics for its use.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments, which would come within the spirit and scope of the present invention.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should be at least construed in light of significant digits and by applying ordinary rounding.

What is claimed is:

1. A system for measuring atomic and molecular decomposition products of an energetic event, the system, comprising:
    an absorption spectroscopy gauge comprising:
        a first portion comprising a first optical path, which, includes a first mirror, the first portion attached to an adjustable attachment mechanism; and
        a second portion comprising a second optical path, which includes a second mirror, the second portion attached to the adjustable attachment mechanism such that the first optical path is aligned with the second optical path defining an absorption region between the first portion and the second portion in an aligned path between the first optical path and the second optical path,
            wherein the adjustable attachment mechanism defines a length of the absorption region and adjusting the adjustable attachment mechanism changes this length, and
            wherein the first portion and the second portion each comprises an elongated shape having a tapered shape at one end thereof and one of respective said first optical path and said second optical path; a light source in communication with the first portion; and a time-resolved spectroscopy system in communication with the second portion.

2. The system of claim 1, wherein the light source is in communication with the first portion through a first optical fiber and the time-resolved spectroscopy system is in communication with the second portion through a second optical fiber.

3. The system of claim 1, wherein the time-resolved spectroscopy system comprises a spectrometer in communication with the second portion, a time-resolved detector in communication with the spectrometer and a charge coupled device in communication with the spectrometer.

* * * * *

UNITED STATES PATENT AND TRADEMARK OFFICE
CERTIFICATE OF CORRECTION

| | |
|---|---|
| PATENT NO. | : 7,675,616 B1 |
| APPLICATION NO. | : 11/974000 |
| DATED | : March 9, 2010 |
| INVENTOR(S) | : Joel R. Carney and John Wilkinson |

Page 1 of 1

It is certified that error appears in the above-identified patent and that said Letters Patent is hereby corrected as shown below:

On the Title page, Item (75) Inventors, Line 4, one of the named inventors, should appear as follows:

John Wilkinson

Signed and Sealed this

Seventeenth Day of August, 2010

David J. Kappos
*Director of the United States Patent and Trademark Office*